(12) United States Patent
Discher, Jr. et al.

(10) Patent No.: US 8,333,729 B2
(45) Date of Patent: Dec. 18, 2012

(54) MULTI-DOSE DELIVERY SYSTEM

(75) Inventors: George L. Discher, Jr., Branford, CT (US); William H. Hylton, North Haven, CT (US); Douglas Hanlon, Branford, CT (US); Vincent Mata, III, Monroe, CT (US); Adam Lehman, Northford, CT (US)

(73) Assignee: Polybiotics LLC, West Haven, CT (US)

( * ) Notice: Subject to any disclaimer, the term of this patent is extended or adjusted under 35 U.S.C. 154(b) by 0 days.

(21) Appl. No.: 12/755,027

(22) Filed: Apr. 6, 2010

(65) Prior Publication Data
US 2010/0256554 A1   Oct. 7, 2010

Related U.S. Application Data

(60) Provisional application No. 61/167,315, filed on Apr. 7, 2009.

(51) Int. Cl.
*A61M 13/00* (2006.01)
(52) U.S. Cl. ........................................................ 604/58
(58) Field of Classification Search .................... 604/58, 604/60, 61, 62; 433/89, 90
See application file for complete search history.

(56) References Cited

U.S. PATENT DOCUMENTS

| | | | |
|---|---|---|---|
| 842,631 A | 1/1907 | Deperdussin | |
| 1,109,072 A | 9/1914 | Kozmousky | |
| 2,502,909 A | 4/1950 | Wick et al. | |
| 2,620,796 A | 12/1952 | Eriksen et al. | |
| 2,850,013 A | 9/1958 | Cordis | |
| 2,883,984 A | 4/1959 | Candido, Jr. et al. | |
| 3,520,299 A | 7/1970 | Lott et al. | |
| 3,638,314 A | 2/1972 | Lopez et al. | |
| 3,650,093 A | 3/1972 | Rosenberg | |
| 4,077,406 A | 3/1978 | Sandhage et al. | |
| 4,569,662 A | 2/1986 | Dragan | |
| 4,576,591 A | 3/1986 | Kaye et al. | |
| 4,673,387 A | 6/1987 | Phillips et al. | |
| 4,726,769 A | 2/1988 | Hirdes | |
| 4,734,261 A | 3/1988 | Koizumi et al. | |
| 4,768,954 A | 9/1988 | Dragan | |
| 4,976,686 A | 12/1990 | Ball et al. | |
| 5,000,886 A | 3/1991 | Lawter et al. | |
| 5,129,825 A | 7/1992 | Discko, Jr. | |
| 5,143,661 A | 9/1992 | Lawter et al. | |
| 5,263,355 A | 11/1993 | Malagnoux | |
| 5,286,257 A | 2/1994 | Fischer | |
| 5,347,998 A * | 9/1994 | Hodson et al. ........... | 128/200.23 |
| 5,366,733 A | 11/1994 | Brizzolara et al. | |
| 5,370,611 A | 12/1994 | Niezink et al. | |

(Continued)

OTHER PUBLICATIONS

International Search Report and Written Opinion for PCT/US2010/030152 dated Jun. 4, 2010, 9 pages.

*Primary Examiner* — Nicholas Lucchesi
*Assistant Examiner* — Aarti B Berdichevsky
(74) *Attorney, Agent, or Firm* — Cantor Colburn LLP

(57) ABSTRACT

According to some embodiments, an apparatus may deliver a medication that comprises a multi-dose syringe, a multi-dose medication storage unit coupled to the multi-dose syringe, and a trigger mechanism. The multi-dose medication storage is to comprise a plurality of pre-loaded doses of a medication where the medication is in powder form. Moreover, the trigger mechanism is to facilitate delivery of one or more of the plurality of doses of the medication from the multi-dose medication storage unit.

12 Claims, 11 Drawing Sheets

U.S. PATENT DOCUMENTS

| | | | |
|---|---|---|---|
| 5,500,228 A | 3/1996 | Lawter et al. | |
| 5,582,162 A * | 12/1996 | Petersson | 128/203.15 |
| 5,622,498 A | 4/1997 | Brizzolara et al. | |
| 5,722,829 A | 3/1998 | Wilcox et al. | |
| 5,817,054 A | 10/1998 | Grimm | |
| 6,047,864 A | 4/2000 | Winkler | |
| 6,083,002 A | 7/2000 | Martin et al. | |
| 6,682,348 B2 | 1/2004 | Lawter et al. | |
| 6,783,534 B2 | 8/2004 | Mehdizadeh | |
| 7,069,929 B2 * | 7/2006 | Young et al. | 128/203.15 |
| 7,699,609 B2 | 4/2010 | Lawter et al. | |
| 2001/0024777 A1 | 9/2001 | Azar et al. | |
| 2005/0058963 A1 | 3/2005 | Stockstill | |
| 2006/0127843 A1 | 6/2006 | Rosenblood et al. | |
| 2006/0259006 A1 | 11/2006 | McKay et al. | |
| 2007/0065769 A1 | 3/2007 | Rohner | |
| 2007/0073267 A1 | 3/2007 | Muller | |
| 2007/0166660 A1 | 7/2007 | Peuker et al. | |
| 2007/0186923 A1 | 8/2007 | Poutiatine et al. | |
| 2007/0243498 A1 | 10/2007 | Wallis | |
| 2007/0259313 A1 | 11/2007 | Dragan et al. | |
| 2008/0044787 A1 | 2/2008 | Cinader, Jr. et al. | |
| 2008/0058732 A1 | 3/2008 | Harris | |
| 2008/0147014 A1 | 6/2008 | Lafferty | |
| 2008/0213720 A1 | 9/2008 | Lewis et al. | |
| 2008/0221510 A1 | 9/2008 | Van Der Graaf et al. | |
| 2008/0299517 A1 | 12/2008 | Delaney, II | |
| 2009/0011031 A1 * | 1/2009 | Staniforth et al. | 424/489 |
| 2009/0139516 A1 * | 6/2009 | Augustyn et al. | 128/200.23 |
| 2009/0163889 A1 | 6/2009 | Cauller et al. | |
| 2009/0233252 A1 | 9/2009 | Cinader, Jr. | |
| 2009/0275000 A1 | 11/2009 | Jung et al. | |
| 2009/0298010 A1 | 12/2009 | Broyles et al. | |
| 2010/0136502 A1 | 6/2010 | Wu et al. | |
| 2011/0017210 A1 * | 1/2011 | Sugianto | 128/203.12 |

* cited by examiner

MULTI-DOSE DELIVERY SYSTEM

CROSS-REFERENCE TO RELATED APPLICATION

This application claims priority to the provisional patent application filed Apr. 7, 2009, having Application Ser. No. 61/167,315 entitled Multi-Dose Delivery System, the contents of which are herein incorporated by reference for all purposes.

BACKGROUND

Periodontitis relates to an inflammatory disease that affects the tissues that surround and support the teeth. Periodontitis may be caused by microorganisms that adhere to and grow on a tooth's surfaces. One way to stop the inflammation is for a patient to receive subgingival antibiotics or other medicants in one or more pockets (i.e., target areas) that are located in the mouth. Similarly, other sites of infection or inflammation present in human dental, medical or animal veterinary applications may require delivery of therapeutic agents to multiple anatomical sites and therefore may also be amenable to multidose delivery.

In conventional delivery devices, antibiotics or other therapeutic agents are delivered a single dose at a time. A conventional delivery device may include a capsule, powder or other dosing form that contains the therapeutic agent or, the conventional delivery device may contain a disposable tip that comprises the agent. When administering more than one dose to a patient, a conventional delivery device must be reloaded between each dose with a new capsule or dosing form or a new tip/agent combination before a next dose is delivered or a next location in the mouth or other anatomical site. Reloading the delivery device each time is not only time consuming, and uncomfortable for the patient, but it may cause treatments to be cost prohibitive for many patients.

SUMMARY

According to some embodiments, an apparatus may deliver a medication that comprises a multi-dose syringe, a multi-dose medication storage unit coupled to the multi-dose syringe, and a trigger mechanism. The multi-dose medication storage units may comprise a plurality of pre-loaded doses of a medication. Moreover, the trigger mechanism may facilitate delivery of one or more of the plurality of doses of the medication from the multi-dose medication storage unit.

DETAILED DESCRIPTION

The several embodiments described herein are solely for the purpose of illustration. Embodiments may include any currently or hereafter-known versions of the elements described herein. Therefore, persons skilled in the art will recognize from this description that other embodiments may be practiced with various modifications and alterations.

Figure 1:
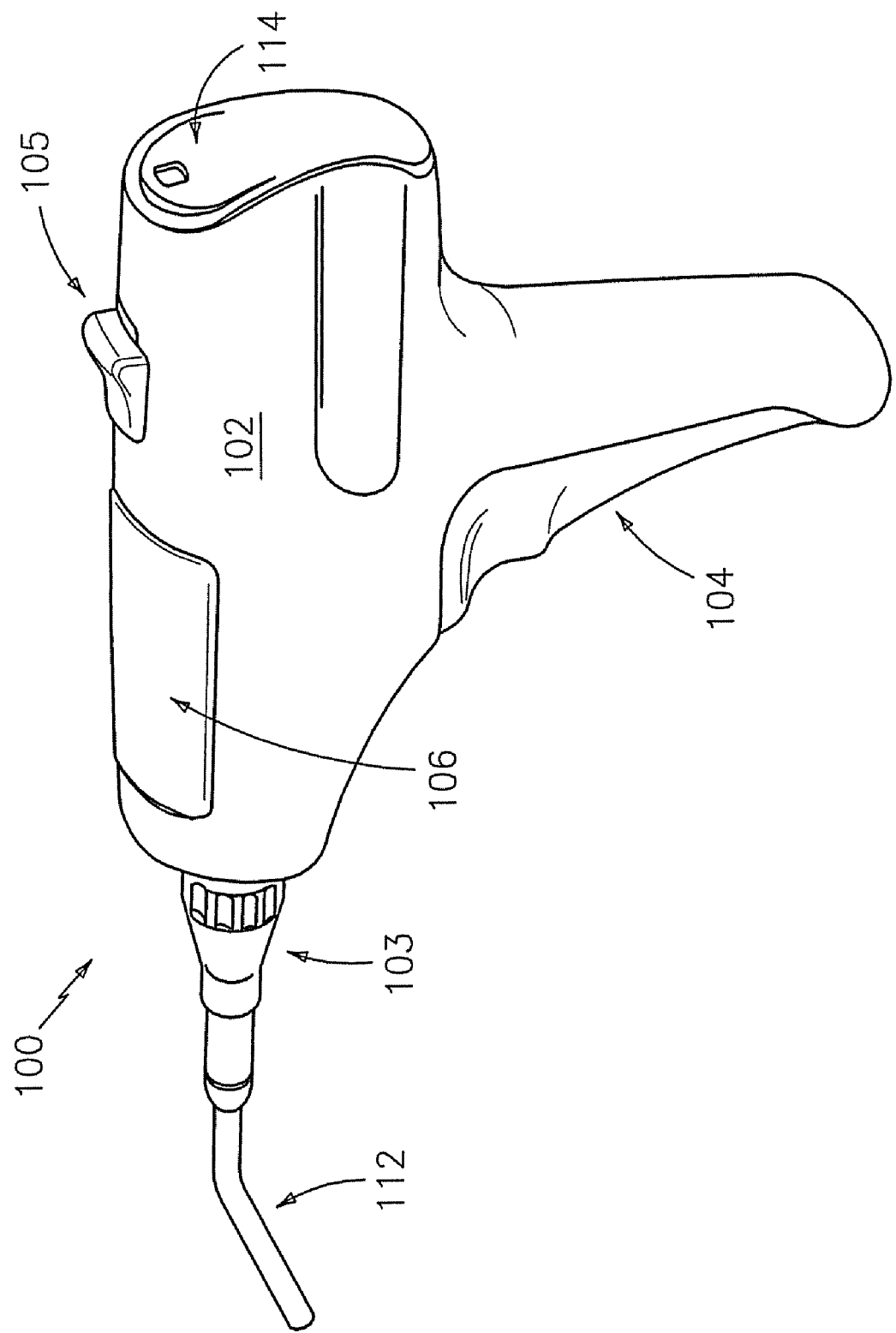
FIG. 1 is a perspective view of one disclosed embodiment.
Figure 2:
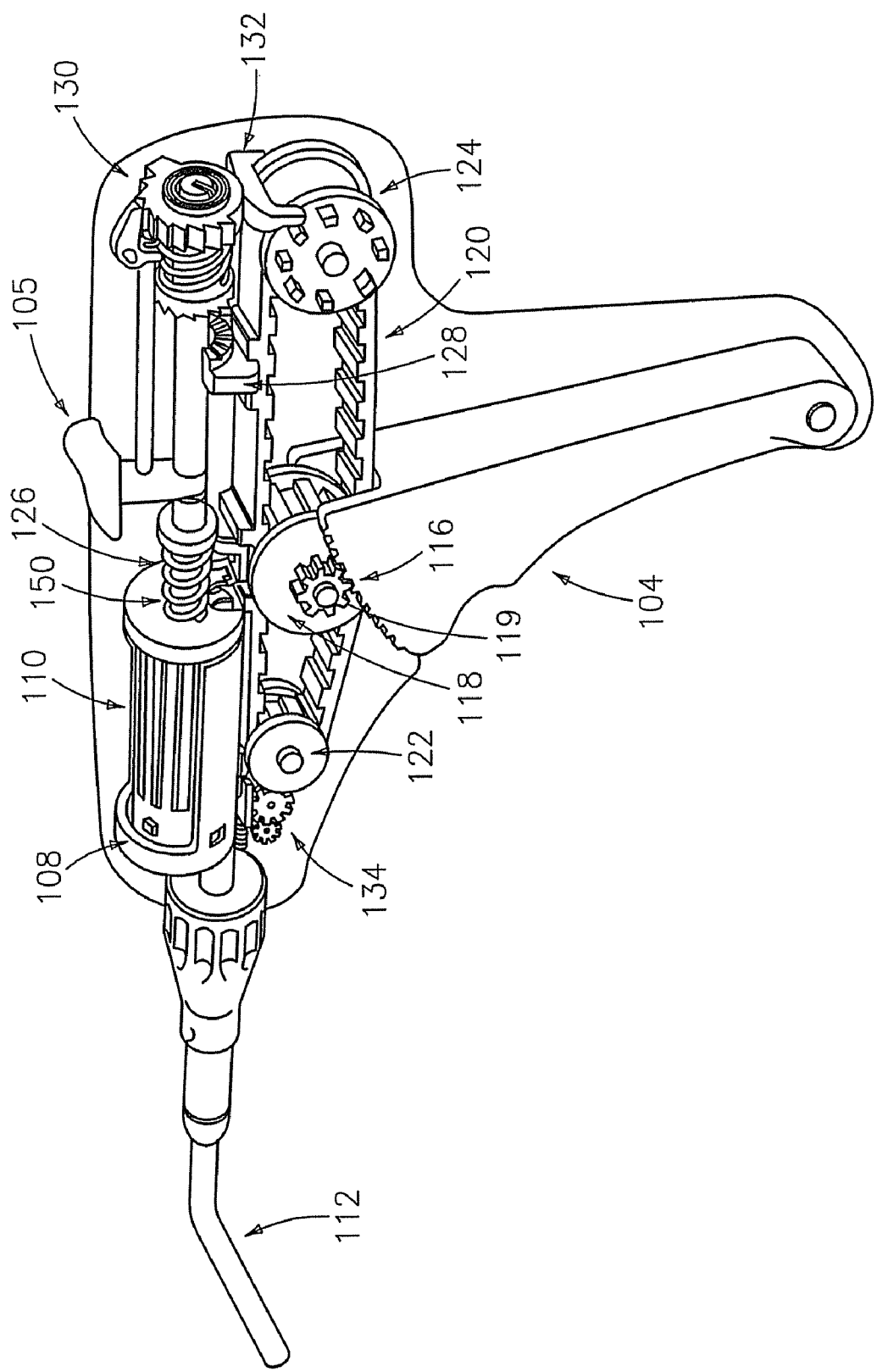
FIG. 2 is a partially cut-away perspective view of the embodiment of FIG. 1.

As shown in FIGS. 1 and 2 a delivery apparatus 100 capable of delivering a plurality of doses of a medication includes a housing 102 and a trigger mechanism 104 movable between a first position (shown) and a second position wherein the trigger is depressed into the housing. A multi-dose cartridge cover 106 is coupled to the housing 102 and covers a magazine cradle 108 that releasably retains a multi-dose medication storage unit 110. A multi-dose syringe 112 is releasably and rotatably coupled to a swivel 103 that is coupled to housing 102 allowing for 360 degree rotation relative thereto. An opening mechanism 105 is movable between an actuated and non-actuated position. Movement of the opening mechanism 105 from the non-actuated to the actuated position will allow the cartridge cover 106 to be opened and, the multi-dose medication storage unit 110 to be replaced. As explained in greater detail below a visual counter indicator 114 indicates a number of doses of medication that have been delivered or amount remaining to be delivered.

The multi-dose syringe 112 comprises a material that is autoclavable and can withstand commonly used disinfectants without degradation of the material. For example, in some embodiments the multi-dose syringe 112 comprises a high-grade plastic, a corrosion resistant metal, or combinations thereof. The trigger mechanism 104 facilitates delivery of one or more of the plurality of doses of the medication from the multi-dose medication storage unit.

Now referring to FIG. 2, an embodiment of a perspective view of the delivery apparatus 100 is illustrated. As illustrated in FIG. 2, a bottom portion of the trigger mechanism 104 is pivotally hinged to a housing 102 of the apparatus 100 and a top portion of the trigger mechanism 104 comprises two rows of gear teeth 116.

A first gear 118 is coupled to the two rows of gear teeth 116. The first gear 118 includes a gear portion 119 that matingly engages the gear teeth 116 defined by the trigger 104. When the trigger 104 is depressed, the gear 118 will rotate. The first gear 118 is coupled to a belt 120. The belt 120 engages a second pulley 122 and a third pulley 124. Therefore, when the trigger mechanism 104 is activated (e.g., the trigger is pressed or pushed), the rotation of the first gear 118 causes the belt 120 to move which in turn causes the second gear 122 and the third gear 124 to rotate in a first rotational direction (e.g., counter-clockwise). Likewise, when the trigger mechanism 104 is deactivated, the movement of the belt 120 causes the first gear 118, the second gear 122, and the third gear 124 to rotate in a second rotational direction (e.g., clockwise). Furthermore, when the trigger mechanism 104 is deactivated and the first pulley 118 rotates, the belt 120 is moved to a home position (i.e., the belt 120 retreats to its original position). In some embodiments, a spring (not shown) returns the trigger mechanism 104 to the above-described first position.

During operation, as the belt 120 moves, it engages a driver plunger 126 and moves it between a neutral position and an actuated position. The driver plunger 126 engages the multi-dose storage delivery unit 110, causing a dose of medication to be delivered. When the belt 120 retreats, the belt 120 disengages the driver plunger 126 allowing the driver plunger 126 to move to its home position and at substantially the same time, advance a shaft turning unit 128 to increment a delivered dose counter 130 and increment the multi-dose storage delivery unit 110.

The shaft turning unit 128 comprises a series of gear teeth, that when coupled to an associated set of gear teeth of the delivered dose counter 130, turn the associated set of gear teeth of the delivered dose counter 130. When the delivered dose counter 130 has been incremented an amount that corresponds to a maximum allowable delivered dose, the delivered dose counter will press on a delivered dose yoke 132 thereby binding the second pulley 124 and preventing the second pulley 124 from turning. Preventing the second pulley 124 from turning prevents the trigger mechanism 104 from being pressed. Some embodiments may provide assurance to a user that an empty multi-dose storage unit will not be used.

Resetting the delivered dose counter 130 requires that a new multi-dose storage unit 110 be placed in the delivery apparatus 100. The multi-dose medication storage unit 110 is removed from the delivery apparatus 100 by engaging the opening mechanism 105 which will activate a biasing means for urging a shaft into a center opening 150 of the magazine 108. In one embodiment, the biasing means may comprise, but is not limited to, a shaft, a plate and a spring to secure the multi-dose medication storage unit 110. Furthermore, engaging the opening mechanism 105 may reset the delivered dose counter 130 as will be explained in more detail with respect to FIG. 4.

When a new multi-dose medication storage unit 110 is placed in the delivery apparatus 100, a multi-dose medication storage unit counter 134 is incremented to count a number of the multi-dose medication storage units 110 that have been associated with (e.g., placed in) the delivery apparatus 100. The multi-dose medication storage unit counter 134 will be described in more detail with respect to FIG. 5.

Figure 3:
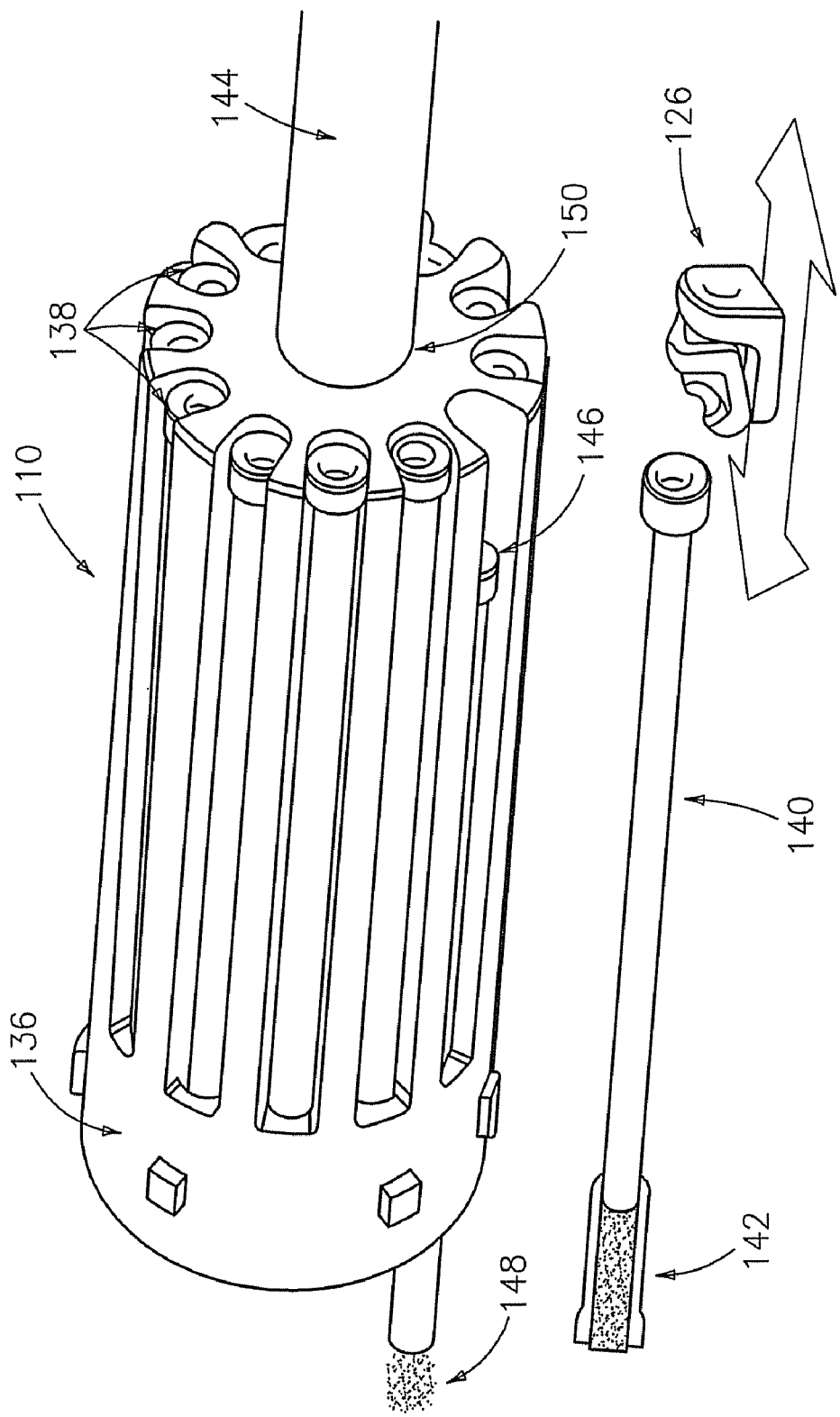
FIG. 3 illustrates a multi-dose medication storage unit that forms part of the embodiment of FIG. 1.

An embodiment of the multi-dose medication storage unit 110 is illustrated in FIG. 3. In some embodiments, the multi-dose medication storage unit 110 is pre-loaded with medication at a factory and/or pharmacy. The pre-loaded multi-dose medication storage unit 110 can be sealed to insure sterility and to prevent moisture from entering the multi-dose medication storage unit 110. The multi-dose medication storage unit 300 comprises a magazine 136 and a plurality of multi-dose bullets 138. The magazine 136 comprises a plurality of grooves and each of the plurality of multi-dose bullets is removably coupled to a respective one of the plurality of grooves of the magazine 136.

Each of the plurality of multi-dose bullets comprises a delivery plunger 140 and a powder cylinder 142. The powder cylinder 142 may comprise a single dose of medication. While the present embodiment describes a powder based medication, any form of therapeutic agent (i.e., particulate, including but not limited to biodegradable micro or nanospheres, liquid, gel, solid or semi-solid scaffold or any of the available matrices in which medicant may be suspended) may also be stored in the powder cylinder 142. When the magazine 136 is turned (i.e., rotated) around a shaft 144 and into a ready position, a non-dispensed multi-dose bullet 138 is aligned with the driver plunger 126. When the driver plunger 126 engages or pushes a delivery plunger, as illustrated with respect to 146, a medication load 148 is dispensed into a multi-dose syringe (not shown). The shaft 144 is coupled to the opening mechanism 105 that is associated with a biasing means for urging the shaft 144 into the center opening 150 of the magazine 108.

After a medication load 148 is dispensed and the trigger mechanism 104 is released, the shaft 144 will be turned via the shaft turning unit 128 and via the belt 120. Turning the shaft 144 advances a next one of the plurality of multi-dose bullets 138 into a ready position as well as increments the delivered dose counter 130. In some embodiments, a number of multi-dose bullets contained in the multi-dose storage unit 110 correspond to a maximum number of doses indicated by the delivered dose counter 130.

Figure 4:
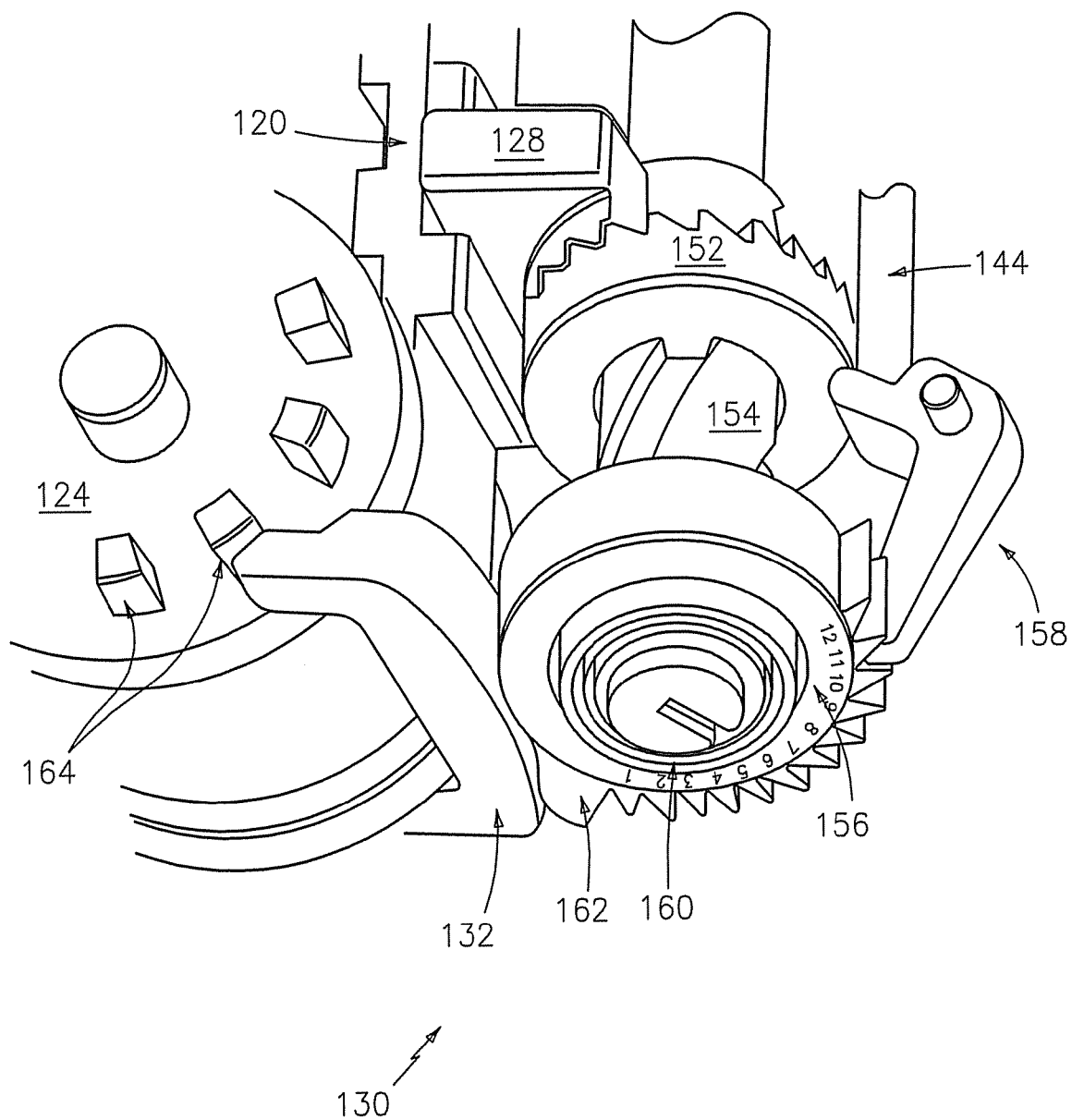
FIG. 4 illustrates a counting mechanism that forms part of the embodiment of FIG. 1.

Now referring to FIG. 4, an embodiment of a delivered dose counter 130 is illustrated. When the trigger mechanism 104 is returned to the home position, shaft turning unit 128 engages trigger engagement gear 152 to turn the indexing spline 154. The trigger engagement gear 152 forces the indexing spline 154 to rotate (e.g., in a clockwise direction). The shaft turning unit 128 comprises a series of gear teeth, that when coupled to an associated set of gear teeth of the trigger engagement gear 152, turn the trigger engagement gear by asserting pressure on the trigger engagement gear's gear teeth.

When the indexing spline 154 turns, a reset pawl 158 is lifted over a gear tooth of a counting gear 156 allowing the reset pawl 158 to be advanced to a next tooth of the counting gear 156. Furthermore, turning the indexing spline 154 may tighten a reset clock spring 160 that is coupled to both the counting gear 156 and to a slot in the indexing spline 154. The reset pawl 158 may prevent the counting gear 156 from turning in a direction opposite of a force of the reset clock spring 160. (i.e., prevent the counter from decrementing).

The counting gear 156 may comprise a fixed number of teeth. For example, in some embodiments the counting gear may comprise 12 teeth and each time a dose of medication is delivered, the reset pawl 158 advances between the first tooth and the twelfth tooth indicating a count between 1 and 12 delivered doses. An inscription on the counting gear 156 gear can be viewed via the visual counter indicator 114 as illustrated in FIG. 1. This inscription can be a count up or count down counter.

When the reset pawl 158 reaches a last tooth of the counting gear 156, the counting gear 156 is in a position such that a cam surface 162 of the counting gear 156 is pressed against the delivered dose counter yoke 132 causing the delivered dose counter yoke 132 to be coupled between two gear stops 164 of the first gear 124.

To uncouple the delivered dose counter yoke 132 from the first gear 204, the opening mechanism 105 is engaged which may push (i.e., move) the reset pawl 158 forward via a shaft 144 causing the reset pawl 144 to be lifted. When the reset pawl 144 is lifted, the counter ring 156 may automatically be turned by the reset clock spring 160 such that the first tooth of the counter ring 156 is aligned with the reset pawl 158. According to some embodiments, a delivered dose counter 156 may allow a user of a multi-dose delivery device to be informed of a number of doses that have been delivered.

Figure 5:
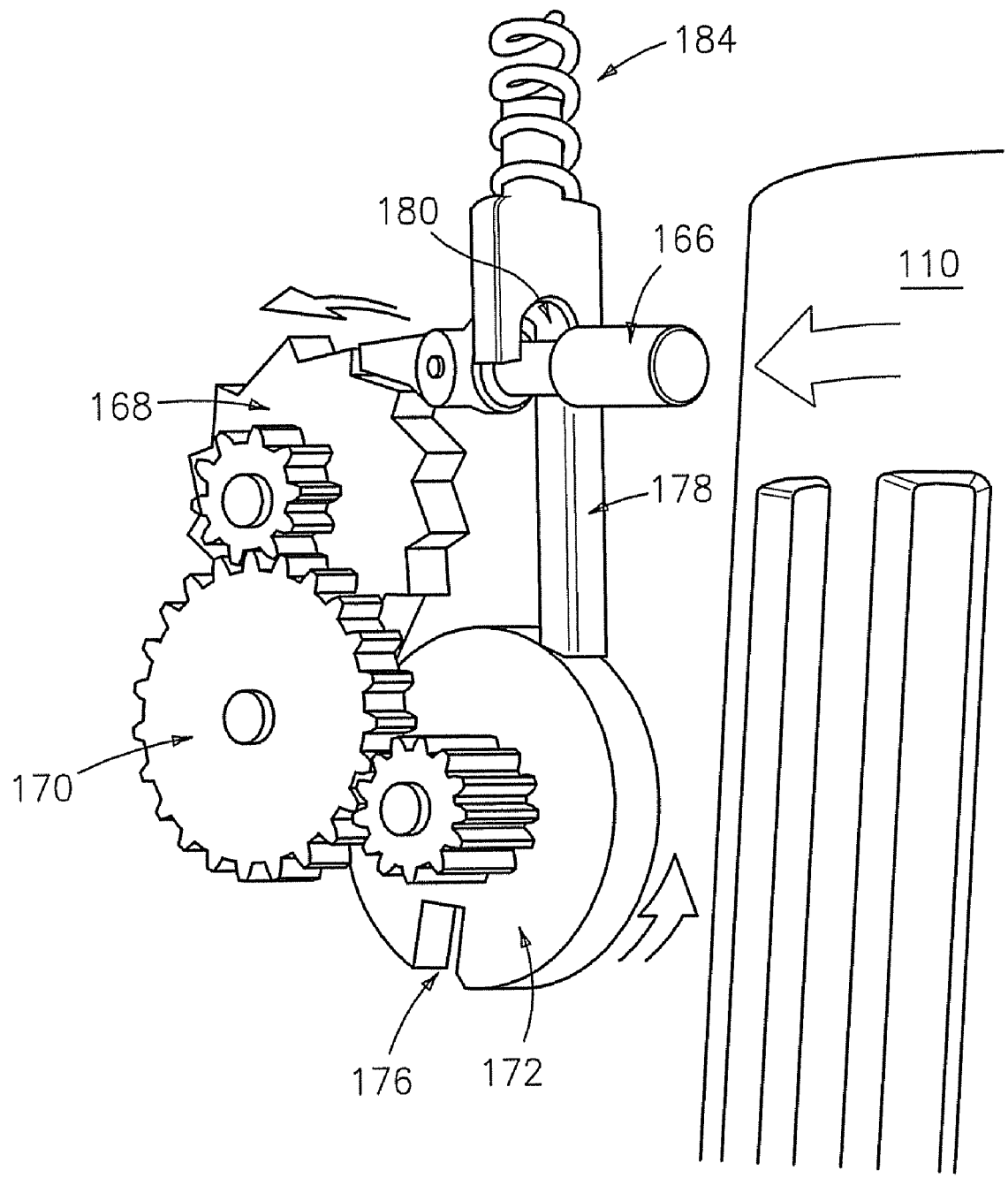
FIG. 5 illustrates another counting mechanism that forms part of the embodiment of FIG. 1.

In some embodiments, a multi-dose apparatus is limited to a fixed number of multi-dose medication storage units. An embodiment of a counting mechanism that may lock out the multi-dose delivery apparatus after a fixed number of multi-dose medication storage units are used is illustrated at FIG. 5.

In some embodiments, each time a multi-dose medication storage unit 110 is loaded into a magazine cradle 108 that holds the multi-dose medication storage unit 110 a pin 166 is depressed. In some embodiments, the pin 166 comprises a top portion and a shaft portion. When the pin 166 is depressed, the pin 166 advances a series of gears 168/170/172 via pawl 174. For example, pawl 174 advances gear 168 which in turn advances gear 170 which in turn advances gear 172. As illustrated, gear 168 may comprise a first set of gear teeth that are coupled to the pawl 174 and a second set of gear teeth that are coupled to gear 170. Gear 170 comprises a single set of gear teeth that are coupled to both gear 168 and gear 172. Gear 172 comprises a first set of gear teeth that are coupled to gear 170 and a non-toothed portion that comprises a slot 176. After a predetermined number of depressions of the pin 166, the slot 176 of gear 172 is aligned with a protrusion 178 of a lock out slide 182. When the slot 176 is aligned with the protrusion 178, the protrusion 178 is advanced into the slot 176 via a biasing means 184 that urges that protrusion 178 into the slot 176. In some embodiments, the biasing means 184 may comprise a compression spring. The protrusion 178 will prevent the gear 172 from turning and will prevent pawl 174 from being able to move. Furthermore, an indent 180 in the lock out slide 182 is inserted between the top portion of the pin 166 and the shaft portion of the pin 166 which prevents the pin 166 from being depressed. Preventing the pin 166 from being depressed may prevent any future multi-dose medication storage units 110 from being inserted into the magazine cradle 108.

Figure 6:
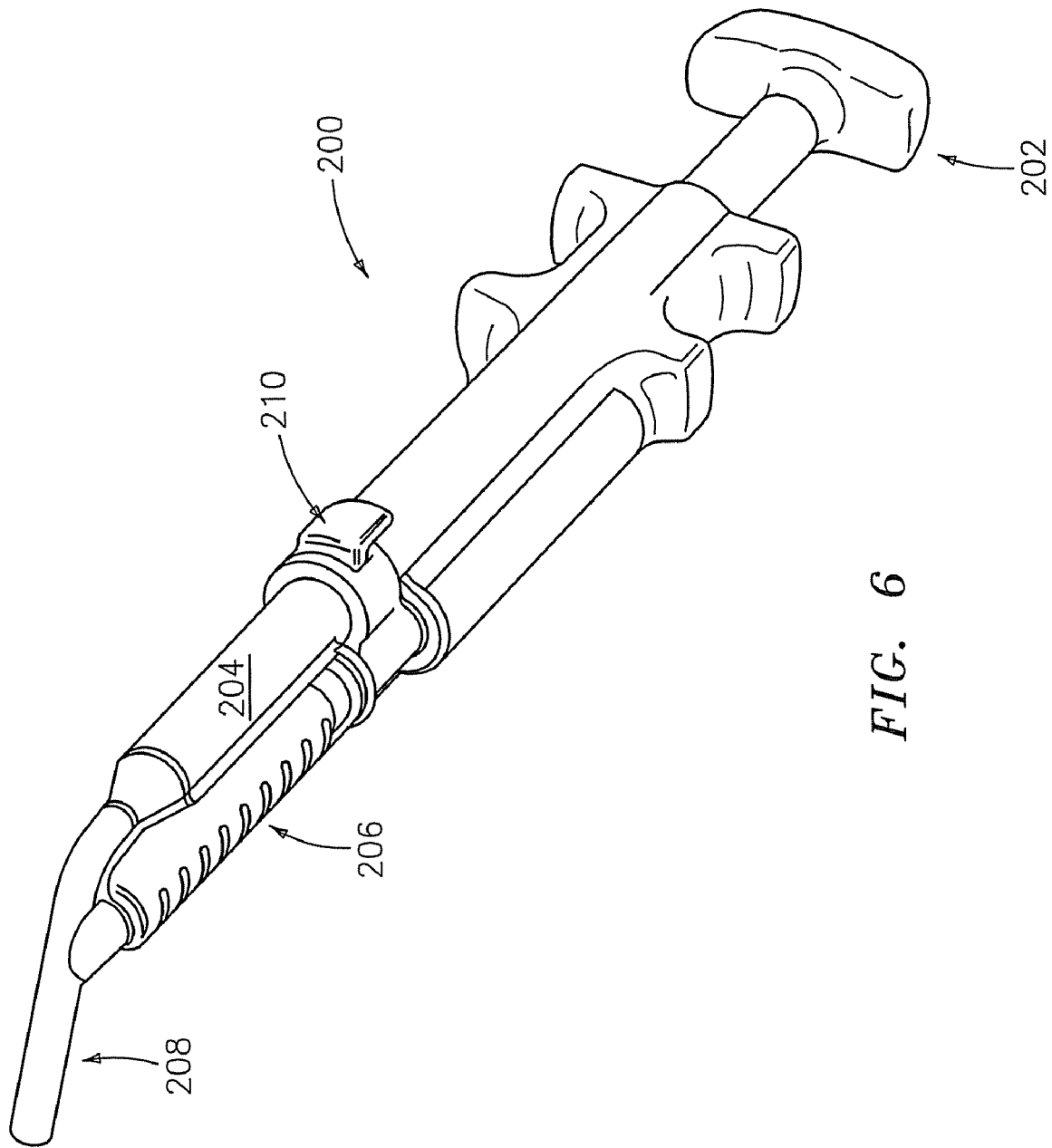
FIG. 6 is a perspective view of another disclosed embodiment.

Referring now to FIG. 6, an embodiment of a delivery apparatus 200 is illustrated. The delivery apparatus 200 comprises a trigger mechanism 202 and a disposable tip portion 204. In some embodiments, the disposable tip portion 204 may comprise a delivered dose indicator 206, a multi-dose syringe 208, and a multi-dose medication storage unit (not shown in FIG. 6). The trigger mechanism 202 is removably coupled to the disposable tip portion 204. The trigger mechanism 202 is uncoupled from the disposable tip portion 204 via release 210. Movement of the release 210 from a non-actuated to an actuated position will allow the trigger mechanism 202 to be separated from the disposable tip portion 204.

Figure 7:
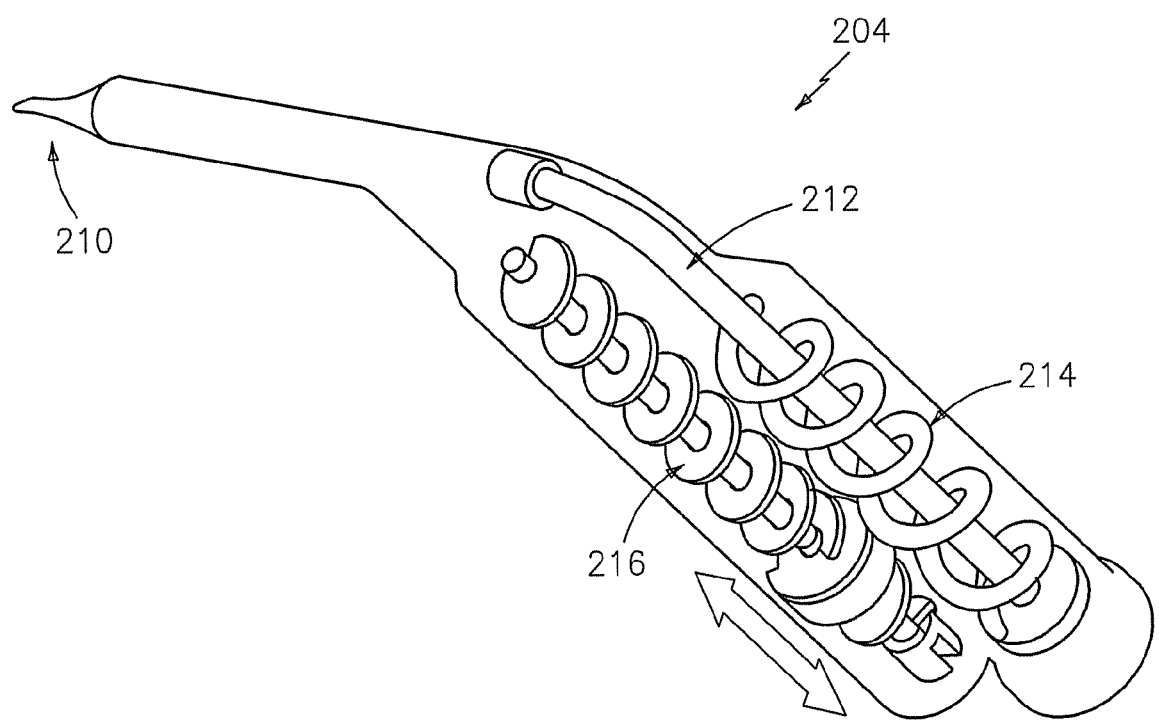
FIG. 7 illustrates a disposable tip portion of the embodiment of FIG. 6.

Now referring to FIG. 7, an embodiment of the disposable tip portion 204 is illustrated. The disposable tip portion 204 may comprise a duck bill valve 210 at an end of a treatment portion of the disposable tip 204. The treatment portion is placed inside a mouth and/or a gum of a patient or at other anatomical sites requiring a dose of therapeutic agent. In some embodiments, the duck bill valve 210 may act as a sphincter by remaining closed until a medication has passed through the duck bill valve 210. When a medication enters the duck bill valve 210, the duck bill valve 210 may expand to encompass the medication until it has passed through the duck bill valve 210 into a target area. When the medication leaves the duck bill valve 210, the duck bill valve 210 may close to prevent moisture from the target area entering the disposable tip portion 204. In some embodiments, the duck bill valve may comprise a rubber or latex based material or other flexible product.

The disposable tip 204 may also comprise a multi-dose medication unit which comprises a flexible plunger 212, a biasing means 214, and an auger 216. In some embodiments, the flexible plunger 212 is advanced into the treatment portion of the disposable tip 204 to deliver a dose of medication through the duck bill valve 210. The biasing means 214 may comprise any biasing means for urging the flexible plunger into both an extended and non-extended position within the disposable tip 204.

In some embodiments, and as illustrated in FIG. 7, the auger 216 may comprise any auger that, when turned, advances a medication towards the duck bill valve 210. In some embodiments, the auger 216 is such that each turn of the auger may provide a single dose of a medication to an area in which the flexible plunger 212 is capable of being extended to push the medication through the duck bill valve 210.

Figure 8:
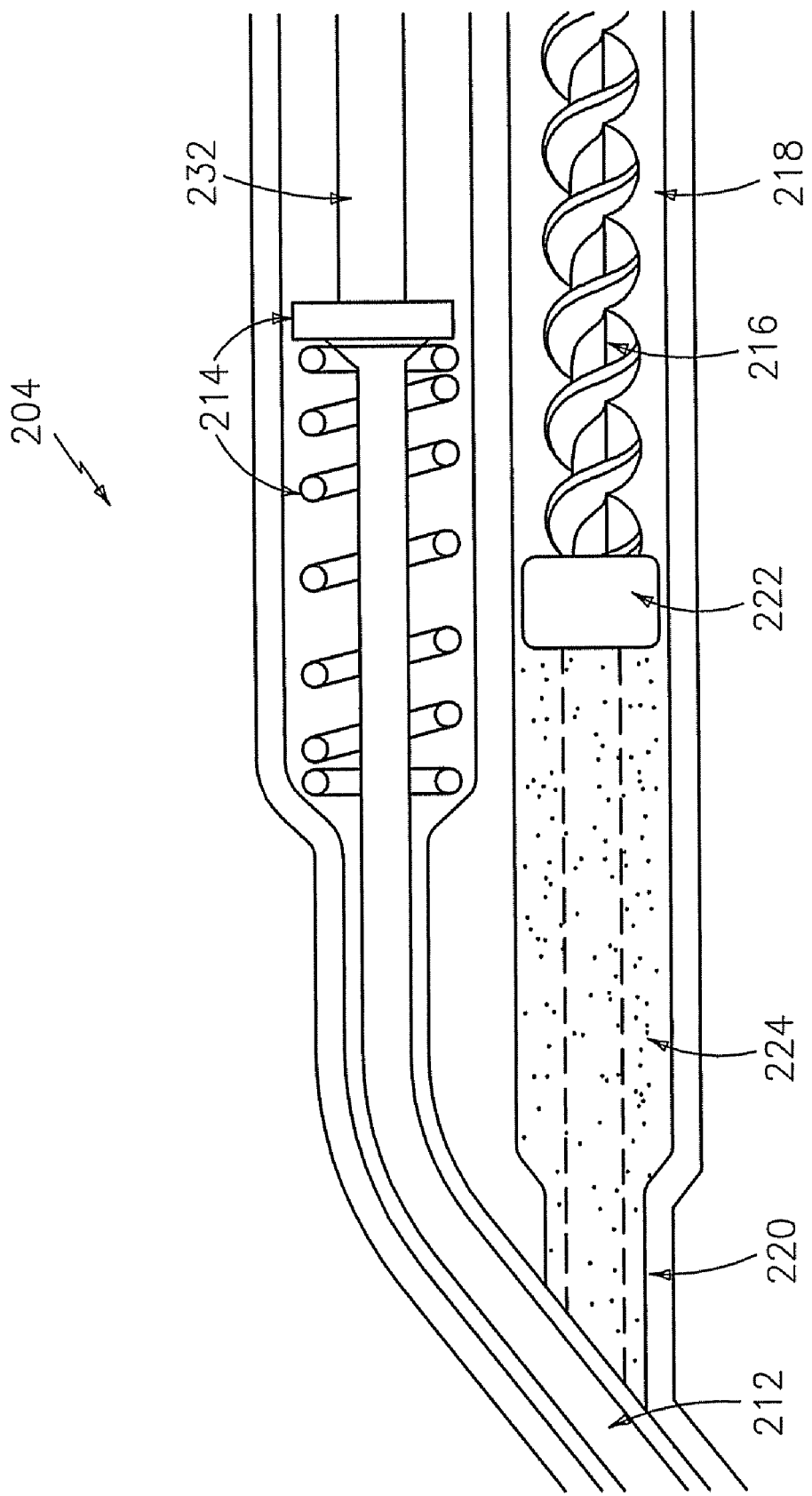
FIG. 8 is a partial cut-away view of a disposable tip portion of the embodiment of FIG. 6.

Now referring to FIG. 8, a disposable tip 204 is illustrated according to some embodiments. In the present illustration, the flexible plunger 212 is illustrated as being extended and being pushed toward the duck bill valve 210. The flexible plunger 212 is pushed via biasing means 214 and via shaft 232. As illustrated, the biasing means 214 comprises, but is not limited to, a plate that compresses a return spring. When the trigger mechanism 202 is released, the biasing means 214 may return the flexible plunger 801 to a starting position by pushing the plate and corresponding shaft 232 with the return spring thus returning the flexible plunger 212 to a home position, such as, but not limited to, a position as illustrated with respect to FIG. 7. Furthermore, and as will be described in more detail with respect to FIG. 9, the shaft 232 may return a handle of a trigger mechanism 202 to a home position.

In some embodiments, the disposable tip 204 may comprise an auger 216 such as, but not limited to, a screw type device that is capable of moving a substance. The auger 216 may extend through a chamber that stores the multi-doses of medication as illustrated by the dashed lines. For purposes of illustration in FIG. 8, the chamber is illustrated as comprising less than a full amount of medication 224. The chamber may comprise a first chamber portion 218 and a second chamber portion 220. The first chamber portion 218 may comprise a radius that is greater than a radius of the second chamber portion 220. In some embodiments, the second chamber portion 220 may function as a metering chamber which corresponds to a single dose of the medication 224.

The auger 216 may further comprise a pushing nut 222 to facilitate pushing of the medication 224 towards the second chamber portion 220. In some embodiments, the pushing nut 222 will move along the auger 216 as the auger 216 turns. The pushing nut 222 is visible through the disposable tip portion 204 and serves as a moving indicator for the dosage delivered indicator 206. In some embodiments, to avoid over compression of the medication 224, the auger 216 protrudes into the second chamber portion 220 to turn the medication 224 in the second chamber portion 220. The medication 224 is more precisely metered in the second chamber portion 220. When the pushing nut 222 reaches the second chamber portion 220, the powder auger 216 stops turning and prevents the trigger mechanism 202 (e.g., a handle 226) from being advanced.

Figure 9:
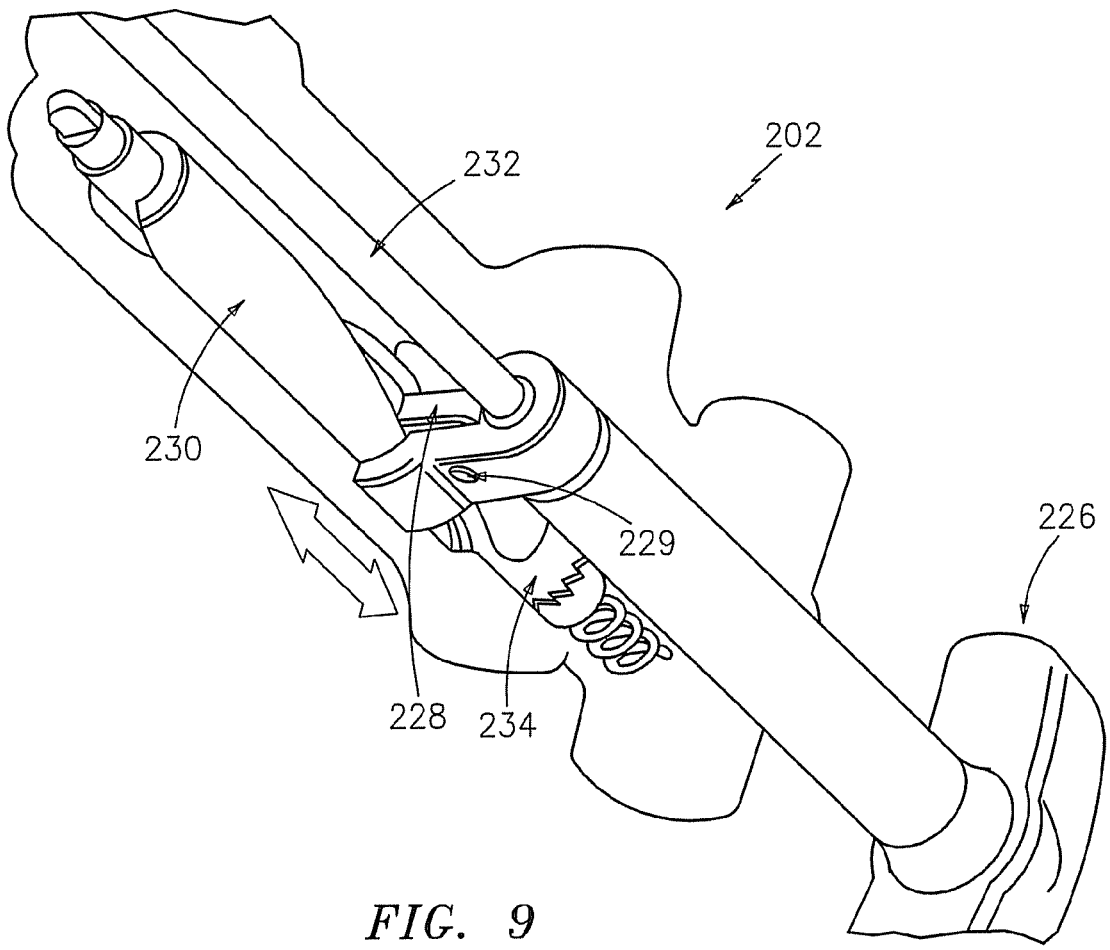
FIG. 9 is a partial cut away view of a trigger mechanism of the embodiment of FIG. 6.
Figure 10:
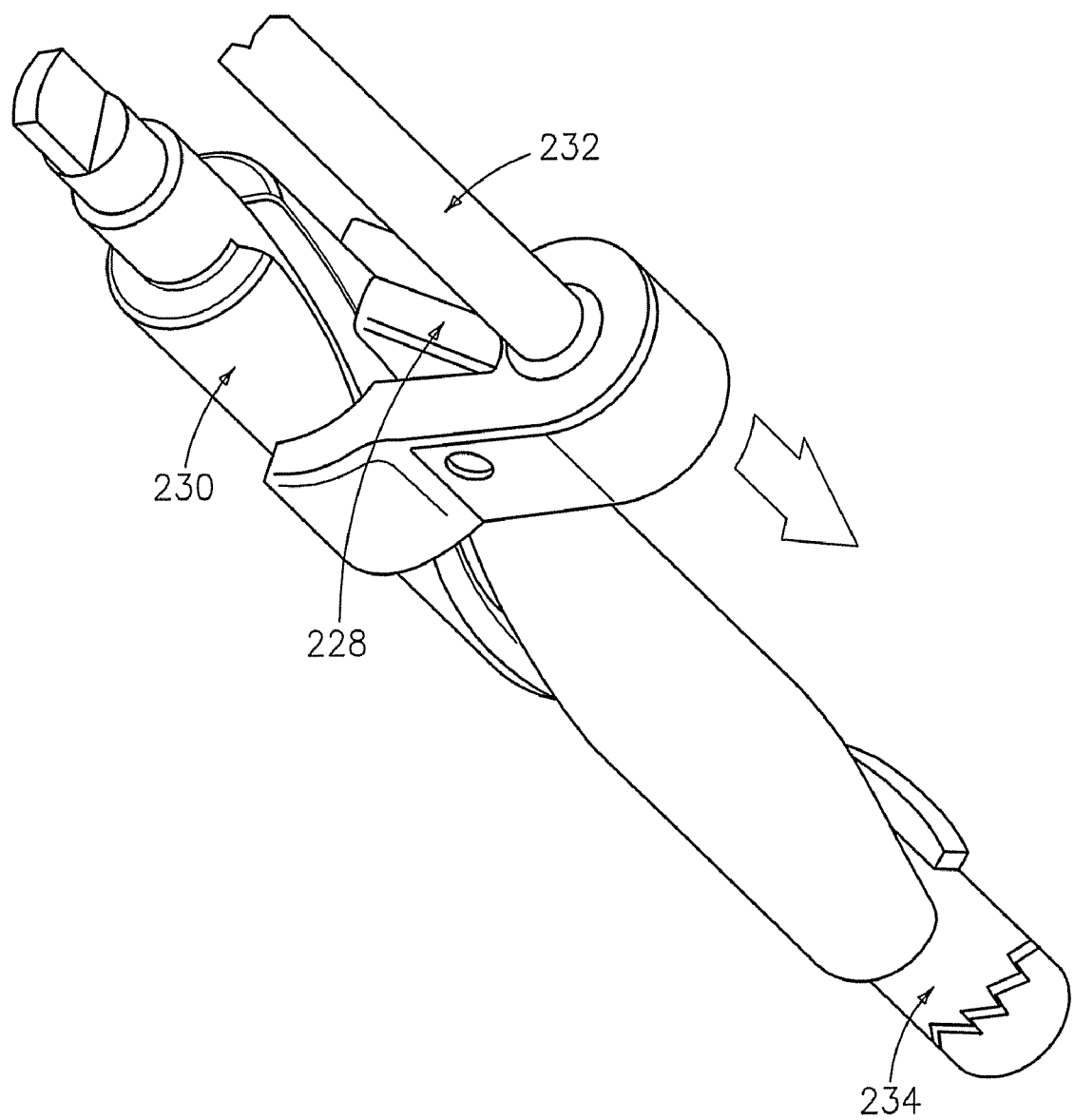
FIG. 10 is an enlarged view of the trigger mechanism of FIG. 9.

An embodiment of the trigger mechanism 202 is described with respect to FIG. 9 and FIG. 10. The trigger mechanism 202 may comprise the handle 226 that when pushed forward will move a drive pawl 228 along a groove in a plunger spindle 230 to turn the plunger spindle 230. The plunger spindle 230 is coupled to the auger 216 and the plunger spindle 230 turns the auger 216. The plunger spindle 230 is configured to allow the auger 216 to turn only in one direction and a finite amount. The shaft 232 is coupled to the flexible plunger 212 to push the flexible plunger 212. Furthermore, the shaft 232 may return the handle 226 to a home position when the shaft 232 is pushed in an opposite direction than when it pushes the flexible plunger 212. Drive pawl 228 is pinned in place via pin 229 and the drive pawl 228 is allowed to pivot around the pin 229. The pivoting motion allows the drive pawl 228 to engage the plunger spindle 230 in a forward direction and disengage the plunger spindle 230 in a reverse direction.

The trigger mechanism 202 may further comprise an anti-reversing mechanism 234. As illustrated in FIG. 10, the shaft 232 may have been pushed by the biasing means 214. As the shaft 232 is pushed by biasing means, the drive pawl 228 disengages from the plunger spindle 230. Plunger spindle 230 may further be prevented from turning by the anti-reversing mechanism 234.

As illustrated in FIG. 10, the anti-reversing mechanism 234 may comprise a series of teeth oriented in a direction to facilitate the plunger spindle 230 turning in a first direction and preventing the plunger spindle 230 from turning in a second direction. In some embodiments, the anti-reversing mechanism 234 may be biased against the plunger spindle 230 via a spring or other flexible device. The drive pawl 228 reengages the plunger spindle when a direction of the shaft 232 is reversed to administer a next dose of medication. For example, the drive pawl 228 may be pushed in a forward motion until it moves along the groove in the plunger spindle 230.

Figure 11:
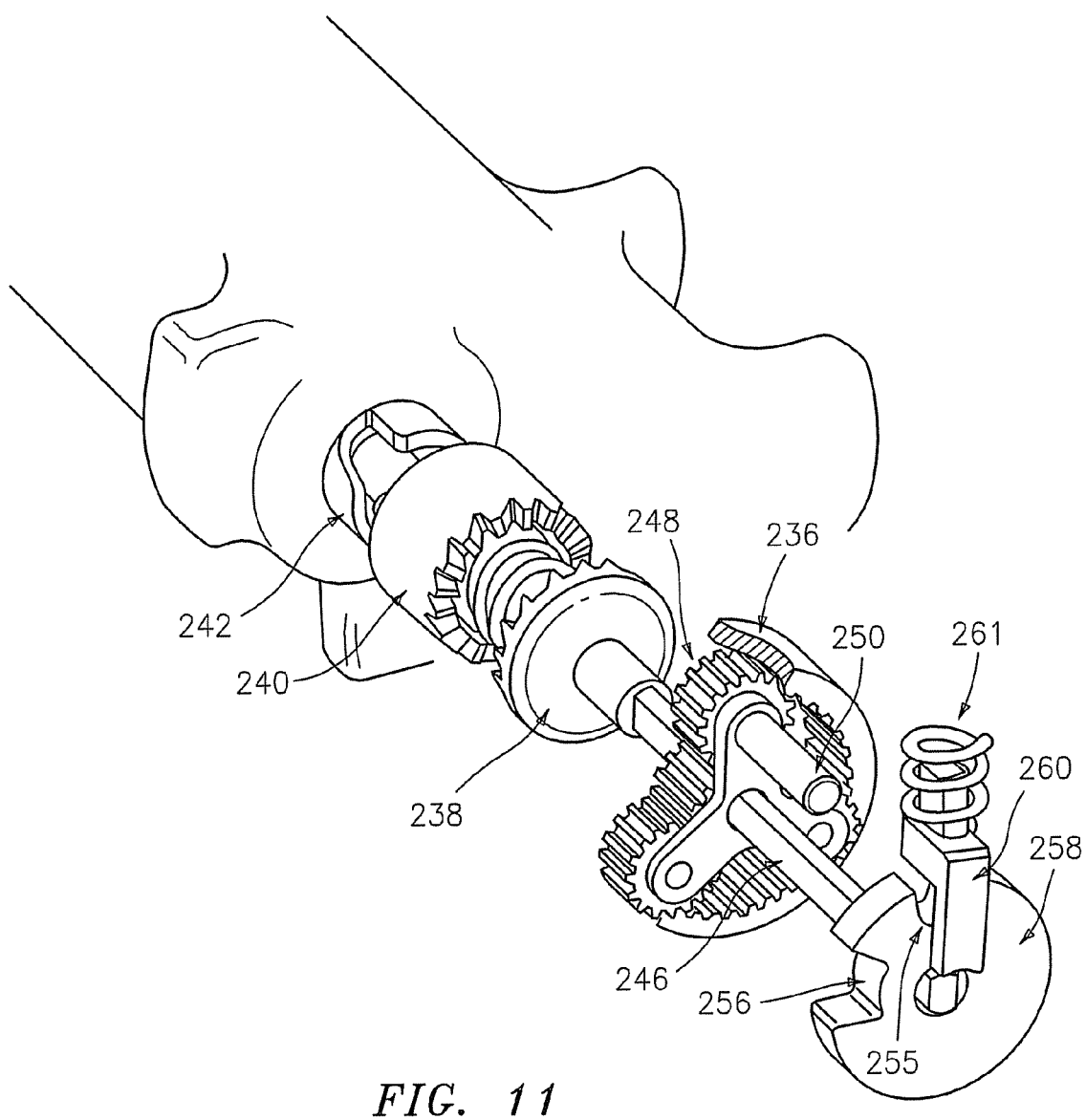
FIG. 11 is an exploded view of a counting mechanism of the embodiment of FIG. 6.

Now referring to FIG. 11, a counter mechanism 244 is illustrated according to some embodiments. In some embodiments, the counter mechanism 244 is incorporated into a plunger portion of the delivery apparatus 200. The counter mechanism 244 counts a number of disposable tip portions 204 that have been associated with the plunger portion. When a new disposable tip 204 is coupled to the trigger mechanism 202, a first pin 246 is depressed which turns a sleeve 242.

In some embodiments, the counter mechanism 244 comprises the sleeve 242 that comprises a plurality of splines. For example, the number of splines may comprise, but is not limited to, 8. An insert 240 is coupled to the sleeve 242. The insert 240 may comprise a first plurality of teeth. The insert 240 may engage a shaft 238. The shaft 238 may comprise a second plurality of teeth to couple the insert 240. In some embodiments, the first plurality of teeth is larger than the second plurality of teeth. In some embodiments, the shaft may rotate in ⅛ of a turn increments.

The shaft 238 is coupled to a planetary gear set 248 and the planetary gear set 248 is coupled to a ring gear 236. The planetary gear 248 may comprise a pin 250 that rotates. Pin 250 is engaged in slot 255 which drives gear blank 258 axially around shaft 246. When slot 256 aligns with slide 260, bias spring 261 pushes slide 260 towards the slot. The slide at this point interferes with shaft 246 because disposable cartridge 204 is still in position. When spent disposable cartridge 204 is removed, shaft 246 advances forward thereby allowing slide 260 to advance forward to fully engage slot 256. In this position, shaft 246 is restricted by slide 260 which prevents the next cartridge from being loaded. The handle 202 is now locked and at the end of its useful life and must either be disposed of or returned to the manufacturer for reconditioning. The several embodiments described herein are solely for the purpose of illustration. Persons in the art will recognize from this description that other embodiments may be practiced with modifications and alterations, limited only by the claims.

What is claimed is:

1. An apparatus to deliver a medication comprising:
   a multi-dose handle member;
   a multi-dose medication storage unit removably coupled to the multi-dose handle member, the multi-dose medication storage unit comprising a plurality of pre-loaded doses of a medication, wherein the multi-dose medication storage unit comprises a first channel with a flexible delivery plunger and a separate, non-contiguous second channel with said medication and a medication feeding member configured to feed the medication through the second channel, said first and second channels merging at a common tip configured to dispense medication supplied from said second channel via said flexible delivery plunger contained in said first channel; and
   a trigger mechanism to facilitate delivery of one or more of the plurality of doses of the medication from the multi-dose medication storage unit.

2. The apparatus of claim 1, wherein the medication is in a powder form.

3. The apparatus of claim 1, wherein the trigger mechanism comprises an anti-reverse mechanism.

4. The apparatus of claim 1, wherein the multi-dose apparatus comprises a duck bill valve at a treatment end of the multi-dose apparatus.

5. The apparatus of claim 1, further comprising:
   a visual indicator to determine a number of delivered doses.

6. The apparatus of claim 1, wherein the second channel comprises a first portion and a second portion, and wherein the second portion comprises a radius that is greater than a radius of the first portion.

7. The apparatus of claim 1, wherein said medication feeding member is an auger.

8. The apparatus of claim 1, further comprising a first counting mechanism to count a number of delivered doses.

9. The apparatus of claim 8, wherein the first counting mechanism is to prevent the apparatus from functioning after a preset number of doses have been delivered.

10. The apparatus of claim 9, wherein the first counting mechanism is reset upon replacement of the multi-dose medication storage unit.

11. The apparatus of claim 8, further comprising:
    a second counting mechanism to count a number of multi-dose medication storage units associated with the apparatus.

12. The apparatus of claim 11, wherein the second counting mechanism is to prevent the apparatus from functioning after a preset number of multi-dose medication storage units have been associated with the apparatus.

* * * * *